United States Patent [19]

Saeda et al.

[11] 4,107,979
[45] Aug. 22, 1978

[54] METHOD AND DEVICE FOR MEASUREMENT OF ENVIRONMENTAL STRESS CRACKING

[75] Inventors: Shigeru Saeda; Yukinori Suzaka, both of Oita, Japan

[73] Assignee: Showa Denko K.K., Tokyo, Japan

[21] Appl. No.: 775,560

[22] Filed: Mar. 8, 1977

[30] Foreign Application Priority Data

Mar. 11, 1976 [JP] Japan .................................. 51-25586

[51] Int. Cl.$^2$ .......................... G01N 3/00; G01N 3/20
[52] U.S. Cl. ...................................... 73/88 R; 73/100
[58] Field of Search .................. 73/88 R, 100, 91, 103

[56] References Cited

U.S. PATENT DOCUMENTS

| | | | |
|---|---|---|---|
| 1,499,546 | 7/1924 | Oxley | 73/91 |
| 2,452,588 | 11/1948 | McFarland | 73/100 |
| 2,506,048 | 5/1950 | van den Akker | 73/100 |
| 2,670,624 | 3/1954 | Faris et al. | 73/100 |
| 3,440,868 | 4/1969 | Boyles | 73/88 R |
| 3,538,757 | 11/1970 | Osborne | 73/100 |

*Primary Examiner*—Anthony V. Ciarlante
*Attorney, Agent, or Firm*—Oblon, Fisher, Spivak, McClelland & Maier

[57] ABSTRACT

Environmental stress cracking of a given material is measured by a method comprising the steps of deforming a test piece of said material for thereby producing stress therein, placing the deformed test piece in a test environment, externally applying thereto stress of a magnitude smaller than that of the stress already produced therein until the test piece fractures and clocking the time the test piece stands in said test environment before fracturing. Said measurement is performed by use of a device which comprises means for holding test pieces, loading means for applying stress to said test piece holding means and indicating the displacement of the test piece occurring at the time of its fracture and means for sensing the displacement.

3 Claims, 5 Drawing Figures

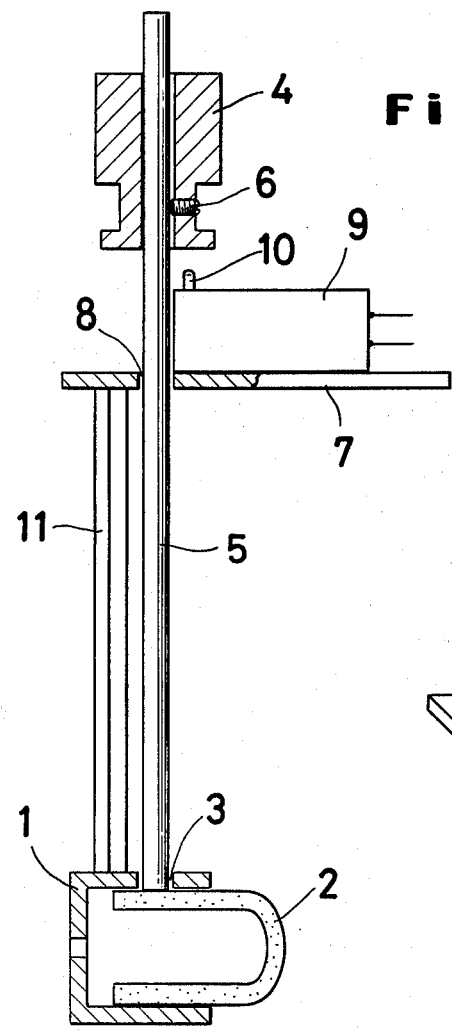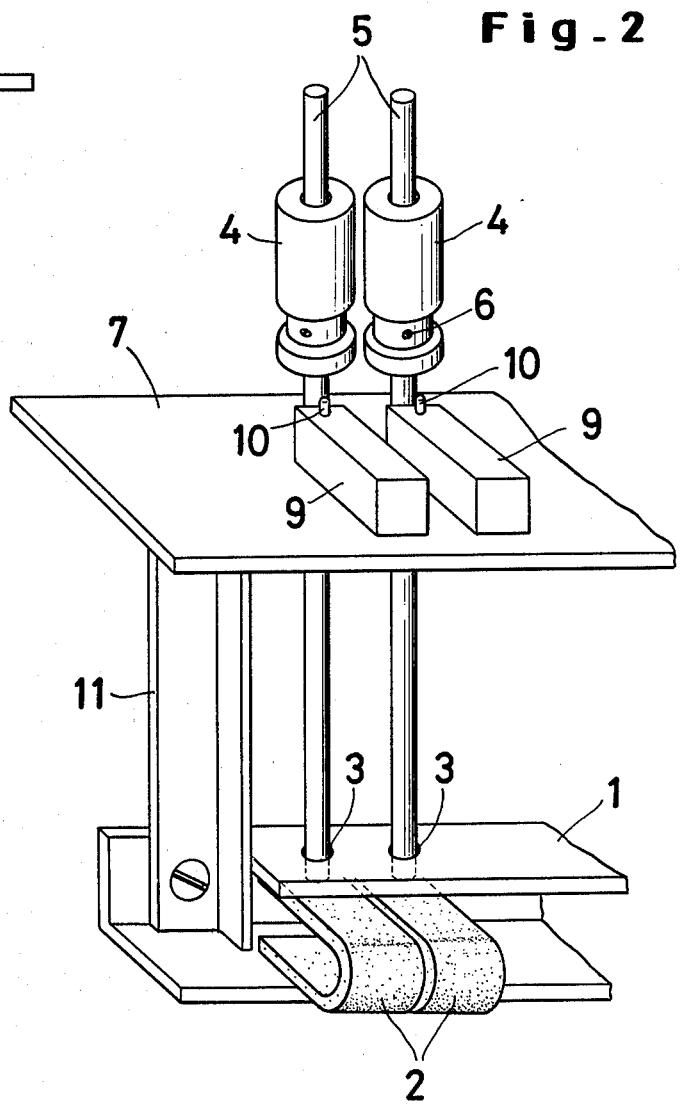

METHOD AND DEVICE FOR MEASUREMENT OF ENVIRONMENTAL STRESS CRACKING

BACKGROUND OF THE INVENTION

This invention relates to a method for the measurement of environmental stress cracking (E.S.C.) mainly occurring in plastic materials or metallic materials and to a device employed for practicing said method.

Whenever a material is put to actual use, it is always exposed to stress of some form or other. This stress at times is exerted directly on the material itself by some external factor. Sometimes it occurs internally in the material because some deforming force is applied thereto. Otherwise it is caused by the strain which remains in the material from the time of its fabrication. Most materials are used in some type of atmosphere (either gaseous or liquid) and, depending upon the kind of material, the kind of atmosphere and the magnitudes of the stress, some sustain cracks so seriously as to be rendered unserviceable in very short periods of time. This phenomenon is called "environmental stress cracking" or "environmental stress fracture" and is highly significant in the practical use of materials. A number of methods have been suggested for expressing the phenomenon in numerical terms. Broadly these are classified under two types: (1) methods wherein a prescribed deformation is imparted to the test piece in advance, the test piece is placed in an environmental liquid (or gas) at a fixed temperature and the time until the test piece sustains cracks is measured and (2) methods wherein a fixed magnitude of stress is imparted to the test piece prior to conducting the same measurement as above.

Among the methods of the former type is the well known ASTM D-1693-70 method developed by Bell Telephone Laboratory. Among those of the latter type, the Lander method (ASTM D-2552) is famous.

The Lander method comprises the steps of keeping a given test piece under a fixed magnitude of tension in an environmental liquid, detecting a fracture in the test piece and, at that precise moment, stopping a timer and automatically recording the time of said fracture.

The numerical value determined by this method is practically useful under actual conditions of use of a material. However, it is rarely exposed to a fixed magnitude of stress at all times. Since the device adopted for this method is unusually large and can test but a small number of test pieces at one time, the Lander method has not found widespread acceptance.

By contrast, the Bell Telephone method has been widely adopted as the standard method. This method, however, cannot be easily automated. Occurrence of cracks or fractures in the test piece is detected solely by visual evaluation conducted at fixed intervals by human beings. Thus, this method may give rise to large error in the numerical value to be obtained and at any rate requires much time and labor.

An object of this invention is to provide a method for the measurement of environmental stress cracking which is almost completely free from the influence of human error, is highly accurate and even permits automation.

Another object of this invention is to provide a device for the measurement of environmental stress cracking which is almost completely free from the influence of human error, is highly accurate and permits automation.

SUMMARY OF THE INVENTION

To attain the objects described above according to the present invention, there is provided a method which comprises first deforming a given test piece for thereby producing stress in the test piece, placing the test piece in a test environmental liquid or gaseous atmosphere and applying thereto a magnitude of stress smaller than the stress produced in the test piece, holding the test piece under said conditions until it fractures and recording the time which elapses up to the moment of fracture. The device of the present invention serves the purpose of practicing the method of this invention and comprises means for holding said test piece in position, load means for applying a load to the test piece held in position by said means, and means for issuing a signal at the moment that the test piece held in position is fractured and the load means consequently changes its position.

BRIEF DESCRIPTION OF THE DRAWING

FIG. 1 is a longitudinally sectioned view of a typical example of the device of this invention.

FIG. 2 is a perspective schematic view of the device of this invention.

DETAILED DESCRIPTION OF THE INVENTION

Figure 3:
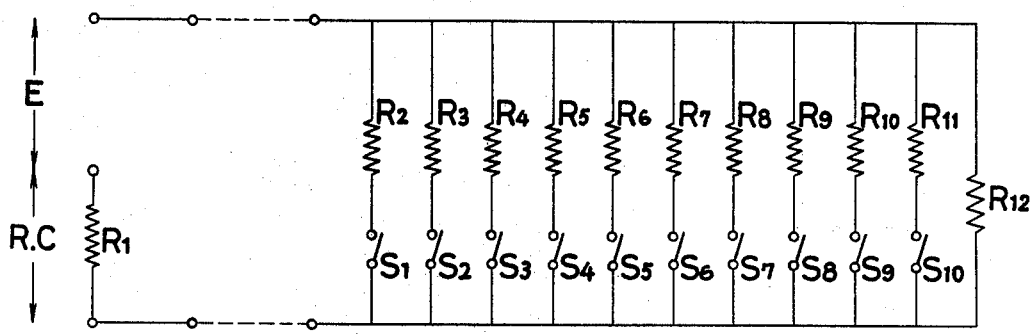
FIG. 3 is the diagram of an electric system of the recorder to be connected to the device of this invention.

Now, the substance of the invention will be described in detail. Generally, when a fixed magnitude of deformation is imparted to a given test piece, it produces a corresponding stress in the test piece. The magnitude of the stress produced in the test piece by a given magnitude of deformation varies with the material of the test piece and the shape thereof. Generally the stress thus produced gradually decreases with elapse of time because of the capacity of the material to alleviate stress. When the material sustains cracks, however, the stress produced in the material precipitously decreases eventually to vanish completely.

The method of the present invention has been perfected on the basis of this principle. Thus, it comprises the steps of deforming a given test piece in advance and thereby producing internally a stress in the test piece, placing the test piece under the environmental atmosphere in which it is to be tested, exerting on the test piece an external stress of a smaller magnitude than the stress already produced in the test piece and recording the time at which the test piece sustains cracks due to the stress. Since the fracture which thus occurs in the test piece can easily be detected in the form of mechanical displacement, this displacement can be utilized to issue a signal. The time which elapses up to the moment the test piece sustains the fracture can be measured, therefore, by having the time of issuance of said signal registered mechanically or electrically. The magnitude of the external stress thus applied to the test piece must be smaller than that of the stress which is produced because of the deformation of the test piece throughout the period of measurement. If the external stress has a larger magnitude, then the test piece is immediately fractured, rendering the measurement meaningless. The magnitude of the external stress, therefore, must be selected by taking into due consideration the numerical value of the stress produced at first in the test piece and the possible decrease of stress due to the inherent capacity of the material to alleviate stress. In view of these requirements, the maximum magnitude of the external stress is limited to less than one half of the stress produced internally in the test piece. If the magnitude of the external stress is too small, then it becomes difficult to determine exactly the precise moment at which the test piece sustains a fracture. All considered, the magnitude of the external stress which proves advantageous for the purpose of this invention is not more than ½ and not less than 1/1000, preferably in the range of from 1/5 to 1/50, of the magnitude of stress produced as described above.

Said signal to indicate the moment that the test piece sustains a fracture can be produced by a method which comprises converting the fracture into a mechanical displacement and then converting the displacement into an electrical phenomenon by the medium of a micro-switch or some other similar contact, an electrostatic inductor or a magnetic inductor or by a method which resorts to use of a mechanical timer. Of the methods available, methods utilizing an electric phenomenon are more advantageous where the registration of fracture must be made efficiently with respect to a multiplicity of test pieces. The deformation of the test piece can be accomplished in any three ways: bending, stretching or twisting. Of the three kinds of deformation, bending most approximates the deformation to which the material is subjected under actual conditions of use and, for this reason, proves to be most favorable. Although the materials to which the present invention is directed are not particularly limited, the invention is effective chiefly on plastic materials, especially on thermoplastic resins such as high-density polyethylene, low-density polyethylene and polypropylene. It can also be used effectively for testing, with respect to durability, those metallic materials which are used in special environmental liquids.

Now, a description will be made of the device used for practicing the method of this invention. FIG. 1 is a longitudinal section of the device of this invention. FIG. 2 is a perspective schematic view of the device of this invention.

In the drawing, 1 denotes a holder for keeping a test piece in position. By 2 is denoted a test piece inserted in position in said holder 1. In the illustrated test piece, the deformation is in the manner of bending. The test piece holder 1 contains an opening 3 through which the interior of the holder communicates with the exterior thereof. Denoted by 4 is a weight which is fastened with a screw 6 onto a shaft 5 extending through the opening 3 of the test piece holder 1 and coming into direct contact with the test piece 2 so as to exert the load of said weight on the test piece 2. By 7 is denoted a supporting plate containing a perforation 8 through said shaft 5 extends. On the supporting plate, there is a weight displacement sensor 9 incorporating an electric contact mechanism (not shown). Denoted by 10 is a weight receiver fastened to the weight displacement sensor. The downward movement of the weight receiver in consequence of the fall of the weight causes the weight displacement sensor to function. By 11 is denoted a support for said supporting plate 7. The heaviness of said weight is fixed depending on the type of the test piece. The electric contact mechanism of the weight displacement sensor is connected to an electric recording unit (not shown).

For testing plastic materials, a device made of stainless steel will suffice. Where the test involves use of an environmental liquid of specifically corrosive nature, the device to be used must be made of material capable of withstanding said corrosive liquid.

Now, the method for measuring the environmental stress cracking by use of the device of this invention will be described. Although two test pieces are illustrated in the drawing, the device may be designed so as to enable a larger number of test pieces to be parallelly set in testing position so that the measurement can be performed on the many test pieces all at once.

As the first step, a test piece deformed in advance to a prescribed shape is set in position in the test piece holder 1. Then, the test piece is placed in its entirety in the required environment. The shaft 5 on which the weight 4 is fastened with a screw is passed through the perforation 8 in the supporting plate 7 and the opening 3 of the test piece holder 1 until the lower end thereof collides against the test piece.

In this case, stress is present in the test piece because of the deformation imparted thereto in advance. The gravitational load which the weight exerts on the test piece must be smaller than the magnitude of the stress thus produced within the test piece, specifically not more than ½ and not less than 1/1000, preferably 1/5 to 1/50, of the stress caused by the deformation. When the test piece is held in this condition, it will eventually sustain a fracture, i.e., it will suffer environmental stress cracking. Consequently, the stress produced within the test piece under the load exerted through the medium of the shaft decreases abruptly and, at the same time, the shaft falls down. The weight comes into contact with the weight receiver 10, which falls down to cause the weight displacement sensor to issue a signal and also cause the electric recording unit to register the time. This registration of the signal in the recording unit can be conveniently accomplished by use of an electric system like the one shown in FIG. 3. The recorder (R.C.) of a full scale rated for 10 mV is used in this case. Shown in the drawing is an electric system adapted to perform the test simultaneously on a total of ten test pieces. In the drawing, $S_1$ through $S_{10}$ are electric contact mechanisms for the ten test pieces, $R_2$ through $R_{11}$ are resistors of 5 KΩ and $R_{12}$ is that of 250 Ω.

A stabilized DC voltage of 25 mV is applied between the terminals E. The recorder indicates the voltage of 1.19 mV where none of the test pieces sustains any fracture. The voltage indicated by the recorder increases to 2.27 mV when one of the test pieces sustains a fracture. As the number of test pieces which sustain fractures increases to 2, 3, ... 10, the voltage indicated increased to 3.26 mV, 4.17 mV, 5.00 mV, 5.77 mV, 6.47 mV, 7.14 mV, 7.76 mV, 8.33 mV and 8.89 mV. Thus, the relation between each number of fractured test pieces and the corresponding time interval is clearly indicated, enabling the operator to read the numerical value of 10% fracture, that of 50% fracture, and so on directly from the recorder. The advantage enjoyed by this circuit is the simplicity in wiring because the device and the recorder need be connected with only two electric wires.

As for the weight displacement sensor, there may be adopted the conventional sensors, such as micro-switches, etc. The conventional electric and mechanical means may be used for the weight displacement sensing and the time recording. That is to say, the present invention is not limited to the preferred embodiment described above.

Now the present invention will be described more specifically below with reference to preferred embodiments.

EXAMPLE 1

In accordance with the method specified by ASTM D-1693-70, 10 test pieces 1 mm in thickness, 38 mm in length and 13 mm in width were prepared by using a high-density polyethylene having a density of 0.962 g/cm$^3$ and a melt index of 9.8 g/10 min. (ASTM D-1238-65T). The 10 test pieces were set in position in the device of the present invention illustrated in FIGS. 1-2. The test piece holder part of the device was immersed in an aqueous 10% (V) solution of a surface active agent (Nonion NS-210 made by Nippon Oils and Fats Co., Ltd., Polyoxyethylenenonylphenolether), at a temperature of 50° C. The contact mechanism of this device was connected to the recorder which was based on the electric system shown in FIG. 3. Since the stress produced in the test pieces at the time of their fabrication was 829 g, the load applied to the test pieces was fixed at 80 g. The ratio of the load to the produced stress, therefore, was 0.096.

By the method of this invention, the 10 test pieces were measured for environmental stress cracking.

Figure 4:
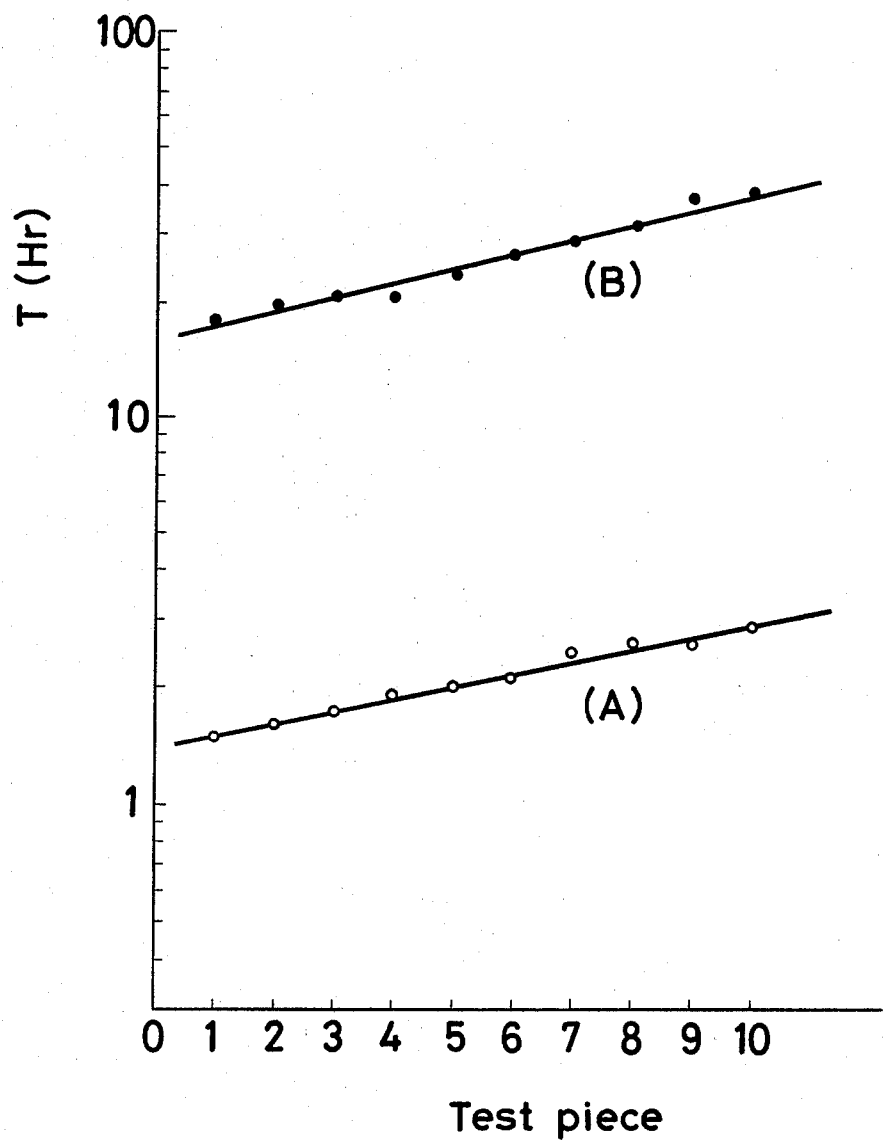
FIG. 4 is a graph showing the results of Examples 1 and 2.

The results were as shown in (A) of FIG. 4. In the graph, the horizontal axis is graduated into ten sections to represent the corresponding ten test pieces and the vertical axis is graduated for the length of time elapsing up to the moment of environmental stress cracking. In the graph, the test pieces are arranged in the chronologic order of fracture.

As is evident from the graph, the points involved very little dispersion, enabling the value of 50% fracture (F50) to be read out easily. To be specific, F50 fell at 2.0 hours.

EXAMPLE 2

Similarly to Example 1, test pieces were prepared by using a high-density polyethylene having a density of 0.957 g/cm$^3$ and a melt index of 0.21 g/10 min. The stress produced in the test pieces at the time of fabrication was 812 g. The load applied to the test pieces was, therefore, fixed at 80 g. The ratio of the load to the produced stress, accordingly, was 0.099.

By following the procedure of Example 1, these test pieces were tested for environmental stress cracking.

The results were as shown in (B) of FIG. 4. Also in the graph, the point involved very little dispersion. F50 fell at 24.3 hours.

EXAMPLE 3

By following the method of ASTM D-1693-70, 60 test pieces 2 mm in thickness, 38 mm in length and 13 mm in width were prepared from a high-density polyethylene having a density of 0.953 g/cm$^3$ and a melt index of 0.21 g/10 min. In this case, a notch 19 mm in length and 0.35 mm in depth was cut at the center (bending portion) of each test piece by an ordinary method. A set each of 10 test pieces was tested for environmental stress cracking by the device shown in FIGS. 1-2, using the same environmental liquid and temperature as those of Example 1. The stress produced in the test pieces at the time of their fabrication was 2600 g, whereas the load applied thereto was fixed at 80 g. This means that the ratio of the load to the produced stress was 0.030. The points involved very little dispersion. F50 was found to fall at 48.5, 48.0, 47.0, 47.0, 47.0 and 46.5 hours.

COMPARISON EXAMPLE

Figure 5:
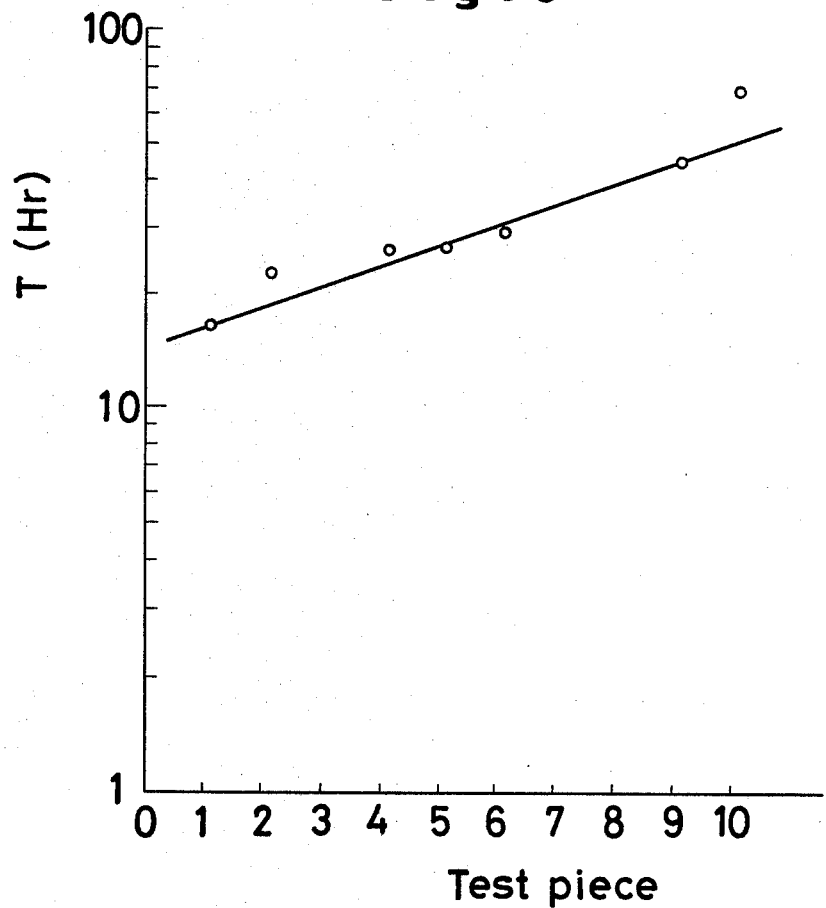
FIG. 5 is a graph showing the results of a Comparison Example.

Test pieces identical in shape with those of Example 3, except the thickness was 3 mm, were prepared from a high-density polyethylene having a density of 0.957 g/cm$^3$ and a melt index of 0.23 g/10 min. by the method of ASTM D-1693-70. These test pieces were placed in the same environmental liquid at the same temperature as in Example 1 in accordance with the method of ASTM D-1693-70 and tested for environmental stress cracking by visual rating. The results were as shown in FIG. 5. The data are found to involve a greater dispersion than those of Examples 1 and 2. F50 fell at 28 HR. For $n = 3$, 7 and 8, the time of fracture could not be measured by the operator. Thus, the data therefor are not included. This is a question attendant upon the visual observation which relies solely upon human faculty.

What is claimed is:

1. A method for the measurement of environmental stress cracking, which comprises deforming a test piece for thereby producing stress in the test piece, determining the magnitude of the stress, placing the test piece in a test environment, externally applying thereto stress of a magnitude fixed at a value smaller than said stress already present in the test piece, keeping the test piece under the applied load until it fractures and, at the moment of the fracture, registering the time required to produce said fracture.

2. The method according to claim 1, wherein the stress externally applied to the deformed test piece is not more than ½ and not less than 1/1000 of the stress present in the test piece.

3. A device for the measurement of environmental stress cracking, which comprises means for holding a test piece in a prestressed deformed position, where said holding means is shaped such that a known prestress is placed on said test piece resulting from a deformation of said test piece required in order for said test piece to be inserted in said holding means, said means incorporating an opening for communication between an inner space thereof and the exterior, loading means consisting of a supporting shaft penetrated through said opening in said test piece holding means and a weight fastened to said shaft, and means for sensing a displacement of said loading means.

* * * * *